(12) United States Patent
Heeney (10) Patent No.: US 6,783,762 B1
(45) Date of Patent: Aug. 31, 2004

(54) PRODUCT AND METHOD FOR OBTAINING SPECIFIC IMMUNIZATION WITH ONE OR MORE ANTIGENS

(75) Inventor: Jonathan Luke Heeney, Voorburg (NL)

(73) Assignee: Stichting Biomedical Primate Research Centre, Rijswijk (NL)

( * ) Notice: Subject to any disclaimer, the term of this patent is extended or adjusted under 35 U.S.C. 154(b) by 0 days.

(21) Appl. No.: 09/890,379

(22) PCT Filed: Jan. 28, 2000

(86) PCT No.: PCT/NL00/00058

§ 371 (c)(1),
(2), (4) Date: Jan. 9, 2002

(87) PCT Pub. No.: WO00/44410

PCT Pub. Date: Aug. 3, 2000

(30) Foreign Application Priority Data

Jan. 28, 1999 (EP) ............................................ 99200256

(51) Int. Cl.[7] .......................... A61K 39/21; A61K 48/00
(52) U.S. Cl. ................. 424/199.1; 424/93.2; 424/207.1; 424/208.1; 514/44
(58) Field of Search ............................. 424/199.1, 93.2, 424/207.1, 208.1; 514/44; 435/320.1

(56) References Cited

U.S. PATENT DOCUMENTS

| | | | | | |
|---|---|---|---|---|---|
| 5,846,546 | A | * | 12/1998 | Hurwitz et al. | ........... 424/202.1 |
| 5,958,895 | A | * | 9/1999 | Pachuk et al. | ................. 514/44 |
| 6,210,663 | B1 | * | 4/2001 | Ertl | ............................ 424/93.2 |
| 6,511,845 | B1 | * | 1/2003 | Davis et al. | ............. 435/320.1 |

FOREIGN PATENT DOCUMENTS

| | | | | |
|---|---|---|---|---|
| WO | 97/06632 | * | 10/1997 | ........... A61K/39/39 |
| WO | WO97/39771 | | 10/1997 | |
| WO | 97/39771 | * | 10/1997 | ........... A61K/39/39 |
| WO | 98/56919 | * | 12/1998 | ........... C12N/15/30 |

OTHER PUBLICATIONS

Papp et al, Viral Immunology 1999, 12 (2) p. 107–116 (Abstract only cited).*
Russell, Journal of General Virology 2000, 81 p2573–2604.*
Mahr et al, Immunological Reviews 1999, 168 p121–130.*
Burgert et al, Current Topics in Microbiology & Immunology 2002, 269 p273–318.*
van Ginkel et al, Journal of Immunology Jul. 15, 1997, 159 (2) p685–93.*
Arribilaga et al, Vaccine Dec. 13, 2002, 21 (3–4) p202–10 (Abstract only cited).*
Jullard et al, European journal of immunology Dec. 1995, 25 (12) p3467–73 (Abstract only cited).*
Fields et al, Molecular therapy Mar. 2000, 1 (3) p225–35 (Abstract only cited).*
Hanke et al. Vaccine 16(5): 439–445, 1998.*
Shengqiang Li, Mauricio Rodrigues, Dolores Rodriguez, Juan Ramon Rodriguez, Mariano Esteban, Peter Palese, Ruth S. Nussenzweig, and Fidel Zavala, "Priming with recombinant influenza virus followed by administration of recombinant vaccinia virus induces CD8+ T–cell–mediated protective immunity against malaria," *Proc. Natl. Acad. Sci. USA* (1993) 90:5214–5218.
Kari R. Irvine, Ronald S. Chamberlain, Eliza P. Shulman, Deborah R. Surman, Steven A. Rosenberg, Nicholas P. Restifo, "Enhancing Efficacy of Recombinant Anticancer Vaccines With Prime/Boost Regimens That Use Two Different Vectors," *Journal of the National Cancer Institute* (1997) 89:1595–1601.
B. Rosenwirth, W.M.J.M. Bogers, I.G. Nieuwenhuis, P. Ten Haaft, H. Niphuis, E.M. Kuhn, N. Bischofberger, V. Erfle, G. Sutter, P. Berglund, P. Liljestrom, K. Uberla, J.L. Heeney, "An anti–HIV strategy combining chemotherapy and therapeutic vaccination," *Journal of Medical Primatology* (1999) 28: 195–205.

* cited by examiner

*Primary Examiner*—Mary E. Mosher
(74) *Attorney, Agent, or Firm*—Hoffmann & Baron, LLP (57) ABSTRACT

A large number of recombinant of viral and bacterial systems has been engineered as vectors to express foreign genes for vaccination and/or gene therapy. A common problem is the immune response to the vector itself. The presence of anti-vector immune response may preclude sufficient priming or delivery if pre-existing immune responses are present, or impair optimal "boosting" upon subsequent immunisation or delivery. The invention provides means and methods for vaccinating an animal or a human to obtain therein an immune response against at least one antigen, comprising different vaccine compositions for sequential administration to said animal or said human, each containing at least said antigen or a precursor thereof, wherein said vaccine compositions differ from each other by the presence therein of a different vector.

11 Claims, 3 Drawing Sheets

PRODUCT AND METHOD FOR OBTAINING SPECIFIC IMMUNIZATION WITH ONE OR MORE ANTIGENS

FIELD OF THE INVENTION

The invention lies in the field of medicine. More particularly the invention relates to vaccines, vaccine compositions and vaccination strategies for obtaining improved immune protection against infectious diseases.

BACKGROUND OF THE INVENTION

The ultimate goal of developing prophylactic and/or therapeutic vaccines for a large number of infectious agents has been difficult to achieve due to the inability to induce optimal immune responses to the pathogen in a safe and effective manner. The previously tried and proven approaches of vaccination with whole killed or live attenuated viruses are either unsafe or ineffective for the remaining infectious diseases of major public health concern. To avoid possible safety problems it has been possible to develop protein based vaccines consisting of one or several individual viral proteins or epitopes thereof. These are derived from individual viral genes expressed in vitro and purified as individual subunits in the protein in the absence of genetic material. Recombinant subunit vaccine approaches have proven effective for certain pathogens such as Hepatitis B. However, for many applications subunit antigens have been unsuccessful due to expression/production difficulties, alteration of relevant immunological epitopes or marked variability of the, pathogen requiring the continuous development, fermentation and purification of new antigens.

Figure 1:
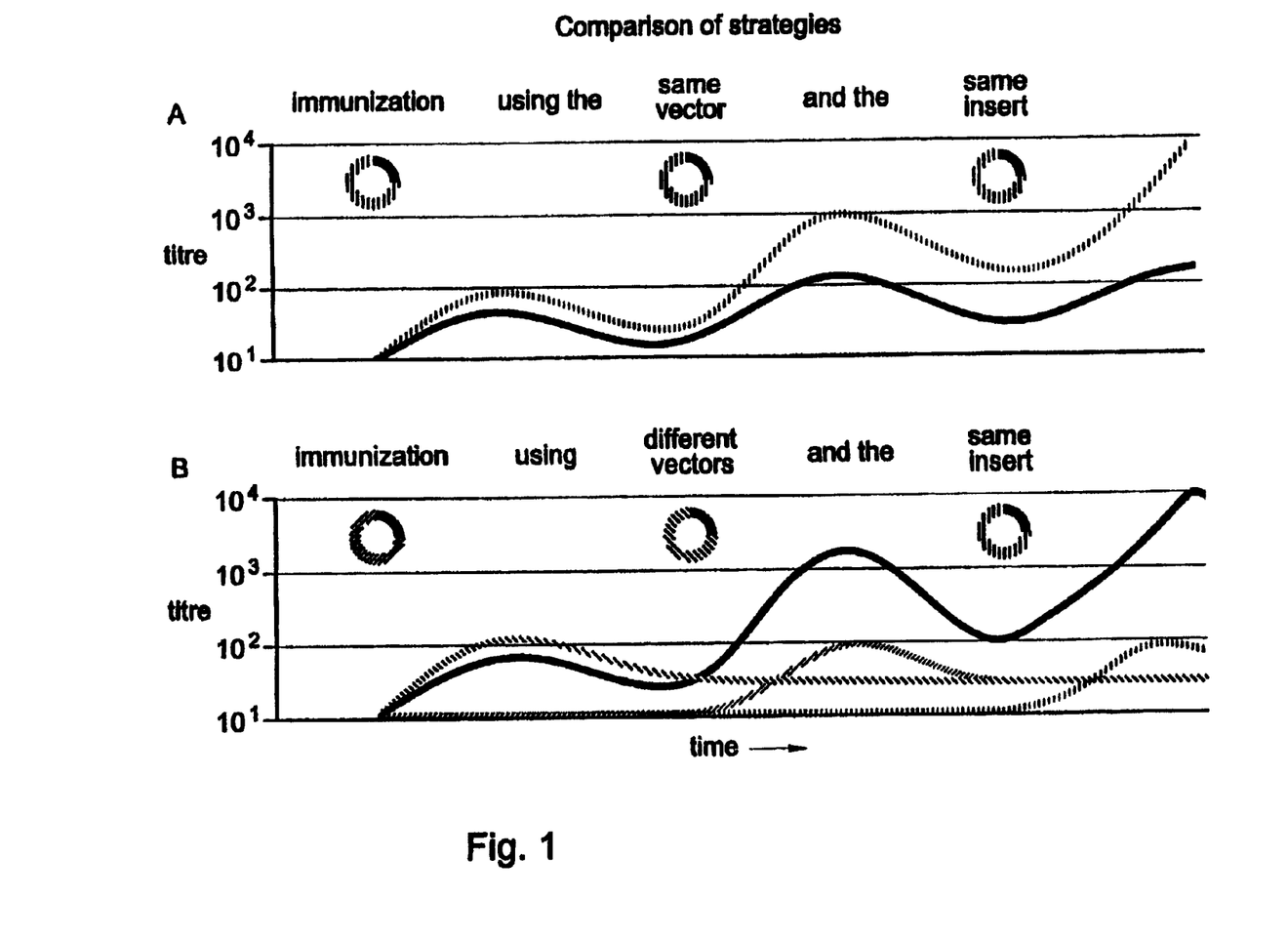

Recombinant live viral or bacterial vaccine vectors were developed as potential solutions to some of these problems. A replicating live virus or bacteria which does not cause disease has the potential to be used as a vector. Attenuated viruses such as adenovirus, poxvirus (i.e. vaccinia, MVA, canary or fowlpox) or bacteria such as *E. coli*, are being developed and evaluated as live vectors. Due to their ability to replicate (in some cases in a limited fashion) in a host without serious side effects, makes them candidate to carry and express foreign genes as "vaccine" antigens. Recombinant vaccines have the advantage that they replicate in the host and thereby induce stronger immune responses than whole killed viruses or bacteria or subunit proteins. An additional advantage is that an immune response to an antigen encoded by said vector, may be improved by the stimulation of the immune system through the presence or the expression of additional proteins, for instance vector specific proteins for instance through providing adjuvant function. However, relatively few, recombinant vector systems alone have been successful enough to be widely accepted for clinical use. Major problems other than safety have been pre-existing immunity in the case of vectors derived from infectious agents common in populations. Furthermore, subsequent immune responses against vector proteins themselves have created a further immunological barrier when more than one immunisation was required to boost responses to the recombinant vaccine antigen (s). One problem is that the immune system may mount an immune response against vector or vector encoded proteins together with an immune response against the antigen, designated the vaccination antigen, the immune response was intended to be directed toward in order to provide the host protection. The observation that the immune system may mount an immune response against a vector protein or a vector encoded protein creates a potential for competition for immune resources such as the availability of immune cells and/or cytokines, thereby lowering the desired response against vaccination proteins (see for example FIG. 1A). Another problem is the potential for more immunogenic antigens present in vector proteins or vector encoded proteins directing the immune response away from vaccination proteins. Additionally, immune responses against the vector eventually limit vector replication in the host, thereby reducing the vectors intended purpose and effectiveness. A problem that specifically increases upon boosting of the immune response with the same or a similar vector or vector system. For instance, the use of different adenovirus serotypes comprising nucleic acid encoding similar vaccination proteins as vaccines is not optimal since the immune system will still be boosted against common antigens present in vector proteins and/or vector encoded proteins. A possible method to avoid this problem is to boost immune responses induced by the recombinant vectors with subunit protein. Several studies have shown that immune responses can be slightly improved by this method but that there is not a substantial improvement in the ability of the vaccine to protect from infection.

SUMMARY OF THE INVENTION

The present invention provides novel means and methods for obtaining a specific immune response in an individual or animal. The invention further provides means and methods for decreasing the negative effects of vector proteins and/or vector encoded proteins while leaving desired effects, such as an adjuvant effect of said proteins at least in part intact (see for a non-limiting example the scheme depicted in FIG. 1B).

In one aspect the invention provides a product for vaccinating an animal or a human to obtain therein an immune response against at least one antigen, comprising at least two different vaccine compositions for sequential administration to said animal or said human, each containing at least said antigen or a precursor thereof, wherein at least two of said vaccine compositions differ from each other by the presence therein of a different vector.

In another aspect the invention provides a method for vaccinating an animal or human to obtain therein an immune response against at least one antigen of a virus causing a temporary, or long lasting immune impairment, comprising administering sequentially to said animal, at least two different vaccine compositions, each containing at least said antigen or a precursor thereof and wherein at least two of said vaccine compositions differ from each other by the presence therein of a different vector.

In yet another aspect the invention provides a use of an antigen, or a precursor thereof, for manufacturing a vaccine composition for vaccinating an animal or a human to obtain therein an immune response against said antigen, wherein said vaccine composition is administered sequentially with at least one other vaccine composition containing at least an immunogenic part, derivative and/or analogue of said antigen or antigen precursor, and a different vector.

DETAILED DESCRIPTION OF THE INVENTION

In one aspect the invention provides a solution to circumvent the negative effects associated with repeated exposure of vector proteins or vector encoded proteins in a vaccination procedure or a vaccine composition. To study problems associated with amplification of an immune response against vector proteins and/or vector encoded proteins a strategy was developed in which the use of different vector systems, to consecutively deliver the same or related antigen(s), was evaluated. The potential existed not only to substantially boost immune responses to the recombinant antigen, but to tailor the nature of the immune responses by priming and then delivering subsequent boosts with different vector combinations or by delivering the vaccine vectors to different immunological sites and/or antigen presenting cell populations. Indeed, the ability to induce preferred type-1 or type-2 like T-helper responses or to additionally generate specific responses at mucosal and/or systemic sites can be foreseen with such an approach.

In one aspect the invention provides means and methods for vaccinating an animal or a human to obtain therein an immune response against at least one antigen of a virus causing a temporary, or long lasting immune impairment, comprising at least two different vaccine compositions for sequential administration to said animal or said human, each containing at least said antigen or a precursor thereof, wherein at least two of said vaccine compositions differ from each other by the presence therein of a different vector. A much better vaccination for such viruses is obtained with at least three different vaccine compositions wherein at least three of said vaccine compositions differ from each other, by the presence therein of a different vector.

In another aspect the invention provides a product for vaccinating an animal or a human to obtain therein an immune response against an antigen comprising at least two different vaccine compositions for sequential administration to said animal or said human, each containing at least said antigen or a precursor thereof, wherein at least two of said vaccine compositions differ from each other by the presence therein of a different vector. An improved vaccination is obtained with at least three different vaccine compositions wherein at least three of said vaccine compositions differ from each other by the presence therein of a different vector. In a vaccination procedure comprising a serial administration to said animal of at least two vaccine compositions comprising at least said antigen or a precursor thereof and wherein at least two of said vaccine compositions differ from each other by the presence therein of a different vector, an amplification of an immune response against vector antigens that may be present in one or more of said vaccine compositions or that may be encoded by nucleic acid present in one or more of said vaccine compositions or both, is at least in part avoided in said animal. By at least in part avoiding said amplification of an immune response against vector antigens in said animal, potential masking of an immune response against said antigen is at least in part prevented. One method of avoiding at least in part an amplification of an immune response against vector antigens in said animal is to avoid at least in part the presence of vector antigens in said animal during said vaccination procedure. This may be achieved for instance by avoiding the presence of vector antigens in at least one of said vaccine compositions or by avoiding at least in part, expression of vector antigens encoded by a nucleic acid in a vaccine composition, or both. Preferably, amplification of an immune response in said animal or human against vector antigens is at least in part prevented by using for said serial administration of vaccine compositions, vaccine compositions comprising different vectors. Another preferred method of avoiding amplification of an immune response against vector antigens in said vaccination procedure is to use at least one vaccine composition useful for avoiding the presence of vector antigens in said animal and at least one vaccine composition comprising a vector. Preferably, when more then one vaccine composition comprising a vector is used, said vector in said vaccine composition is essentially different.

A process for vaccinating an animal or human may be any vaccination process provided that said process utilises serial administration of vaccine compositions containing at least an antigen or a precursor thereof, against which said animal or human should at least in part be vaccinated. Vaccine compositions are preferably administered to said animal or human in an amount effective, for eliciting an immune response in said animal or human.

Said antigen may be a complete protein or a part of a protein. Said antigen may also be, a proteinaceous molecule, derived from nature or synthesised chemically. In one embodiment of the invention said animal is a human.

In one embodiment the invention provides a product for vaccinating an animal or a human to obtain therein an immune response against at least one antigen, comprising at least two different vaccine compositions for sequential administration to said animal or said human, each containing at least said antigen or a precursor thereof, wherein at least two of said vaccine compositions differ from each other by the presence therein of a different vector. Preferably said product comprises at least three of said compositions and wherein at least three of said vaccine compositions differ from each other by the presence therein of a different vector.

In one embodiment at least part of, said vector or a product thereof, functions as an adjuvant. An adjuvant in the context of the present invention is any molecule or combination of molecules, capable of modulating an immune response against said antigen. In one example an adjuvant has the capability to stimulate the immune system in said animal to elicit an immune response wherein said stimulation also stimulates the initiation or the amplification of an immune response against said antigen. In one example, an adjuvant is a classical adjuvant such as complete or incomplete freund adjuvant. In another example said adjuvant is a proteinaceous molecule immunologically different from said antigen, capable of eliciting an immune response in said animal or human.

Preferably said proteinaceous molecule comprises at least a functional part of a co-stimulatory molecule such as CD80, CD86, CD28, CD152, CD40 or CD40 ligand; of a cell-adhesion protein; of an immune response inhibitory protein; of an interleukin; of a major histocompatibility complex protein or of other proteins capable of modulating an immune response. An immune response may be modulated through at least in part inhibiting or preventing an immune response and/or at least in part inducing or enhancing an immune response.

In a preferred aspect of the invention vaccination is be performed together with a method for influencing at least in part immune system, for example in the direction of a preferred T helper 1 type of immune response or a more T helper 2 type of immune response. It is now widely accepted that T cell-dependent immune responses can be classified on the basis of preferential activation and proliferation of two distinct subsets of CD4$^+$ T-cells termed $T_H1$ and $T_H2$. These subsets can be distinguished from each other by restricted cytokine secretion profiles. The $T_H1$ subset is a high producer of IFN-γ with limited or no production of IL-4, whereas the $T_H2$ phenotype typically shows high level production of both IL-4 and IL-5 with no substantial production of IFN-γ. Both phenotypes can develop from naive CD4$^+$ T cells and at present there is much evidence indicating that IL-12 and IFN-γ on the one hand and IL-4 on the other are key stipulatory cytokines in the differentiation process of pluripotent $T_H0$ precursor cells into $T_H1$ or $T_H2$ effector cells, respectively, in vitro and in vivo. Since IFN-γ inhibits the expansion and function of $T_H2$ effector cells and IL-4 has the opposite effect, the preferential expansion of either IFN-γ producing cells (pc) or IL-4 pc is indicative of whether an immune response mounts into a $T_H1$ or $T_H2$ direction. The cytokine environment, however, is not the only factor driving $T_H$ lineage differentiation. Genetic background, antigen dose, route of antigen administration, type of antigen presenting cell (APC) and signalling via TCR and accessory molecules on T cells. In a preferred aspect of the invention the immune system is directed toward a more T helper 1 or 2 type of immune response through using vectors with the property of modulating an immune response in one direction or the other. In a preferred aspect of the invention at least part of said adjuvant function comprises means for directing the immune system toward a more T helper 1 or 2 type of immune response.

Preferably through using vectors with the property of modulating an immune response in one direction or the other. Examples of vectors with the capacity to stimulate either a more T helper 1 or a more T helper 2 type of immune response or of delivery routes such as intramuscular or epidermal delivery can be found in Robinson 1997, Vaccine 15:785–787; Sjolander et al 1997, Cell. Immunol. 177:69–76; Doc et al 1996, Proc. Natl. Acad. Sci. USA 93:8578–8583; Feltquate et al 1997, J. Immunol. 158:2278–2284; Pertmer et al 1996, J. Virol 70:6119–6125; Prayaga et al, Vaccine 15:1349–1352; Raz et al 1996, Proc. Natl. Acad. Sci. USA 93:5141–5145.

In a preferred aspect of the invention the immune system is induced to produce innate immune responses with adjuvant potential in the ability to induce local inflammatory responses. These responses include interferons, -chemokines, and chemokines in general, capable of attracting antigen processing and presenting cells as well as certain lymphocyte populations for the production of additional specific immune responses. These innate type responses have different characteristics depending on the vector or DNA used and their specific immunomodulating characteristics, including such as encoded by CpG motifs, and as such, the site of immunisation. By using in a specific sequence different vectors encoding at least one common specific vaccine antigen, different kinds of desired protective vaccine responses may be generated and optimised for defence from a particular infectious agent. By combining different vector systems and delivering them at different or the same specific sites the desired vaccine effect at a particular site of entry (i.e. oral, nasal, enteric or urogenital) of the specific infectious agent.

In one aspect at least one of said vectors comprises antigen presenting cells, preferably engaged in vivo but also in vitro from said animal. Preferably said antigen presenting cells are dendritic cells. Preferably said antigen presenting cells present said antigen, or an immunogenic part, such as a peptide, or derivative and/or analogue thereof, in the context of major histocompatibility complex I or complex II.

In a preferred embodiment at least one of said compositions comprises as an antigen precursor a nucleic acid encoding at least one proteinaceous molecule for inducing and/or boosting an immune response against said antigen. In a preferred embodiment said nucleic acid is capable of replicating in a cell of the animal or human being vaccinated. With the term boosting in this respect is meant amplifying an immune response such, that when said animal is exposed to said antigen after the amplification, the immune response to said antigen is increased in magnitude compared to before said amplification. Said proteinaceous molecule for inducing and/or boosting an immune response against said antigen may be said antigen or an immunogenic part, derivative or analogue thereof. Alternatively, antigen or an immunogenic part, derivative or analogue thereof may be encoded by a nucleic acid present in said vaccine composition.

In a preferred embodiment said antigen is an antigen encoded by a nucleic acid of a pathogen, preferably of a virus. In a particularly preferred embodiment said antigen is an antigen encoded by a virus which causes a temporary or long lasting immune impairment. For such viruses it has not been possible to devise a satisfactory vaccination strategy to completely protect from infection. The present invention is however, surprisingly suited to provide a satisfactory vaccination for viruses causing different degrees of immune impairment. Some vaccination is obtained using a product comprising at least two different vaccine compositions for sequential administration to said animal or said human, each containing at least said antigen or a precursor thereof, wherein at least two of said vaccine compositions differ from each other by the presence therein of a different vector However, vaccination is substantially improved to provide substantial protection when at least three different vaccine compositions are used for sequential administration to said animal or said human, each containing at least said antigen or a precursor thereof, wherein at least three of said vaccine compositions differ from each other by the presence therein of a different vector.

For effective maintenance and further boosting of the vaccination it is preferred that the immune capacity of the vaccinated individual is boosted at intervals with a vaccine comprising yet another adjuvant. In a preferred embodiment said antigen encoded by a virus causing a temporary, or preferably long lasting immune impairment is an antigen of a lentivirus, another retrovirus, a hepatitis C virus, another flavivirus, a measles virus, another paramyxovirus or a Herpes Virus. In a preferred embodiment said antigen comprises at least an immunogenic part, derivative and/or analogue of a lentivirus gag, pol rev, tat, nef or env protein or a combination thereof.

In a preferred embodiment at least part of said adjuvant function by a vector is provided by a nucleic acid which encodes at least one proteinaceous molecule capable of modulating an immune response. Preferably said nucleic acid is capable of replicating in a cell of the animal of the human being vaccinated. Preferably said proteinaceous molecule capable of modulating an immune response comprises a functional part of a co-stimulatory molecule such as CD80, CD86, CD28, CD152, CD40 or CD40 ligand; of a cell-adhesion protein; of an immune response inhibitory protein; of an interleukin; of a major histocompatibility complex protein or of other proteins capable of modulating an immune response.

In one embodiment the invention provides vaccine compositions wherein said vector is nucleic acid delivery vehicle comprising said nucleic acid. In a preferred embodiment said nucleic acid is capable of replicating in a cell of an animal or human being vaccinated. In a preferred embodiment said replicated nucleic acid has at least a limited capacity to spread to other cells of the host and start a new cycle of replication and antigen presentation and/or present adjuvant function. In a preferred embodiment said nucleic acid comprises nucleic acid of a Semliki Forest Virus, a poxvirus, a herpes virus and/or an adenovirus. In a preferred embodiment said nucleic acid delivery vehicle is a Semliki Forest Virus particle, a pox virus particle, a herpes virus particle or an adenovirus particle.

In another embodiment the invention provides a method for vaccinating an animal to obtain therein an immune response against at least one antigen, comprising administering sequentially to said animal, at least two different vaccine compositions, each containing at least said antigen or a precursor thereof and wherein at least two of said vaccine compositions differ from each other by the presence therein of a different vector. Preferably said animal is a human.

In yet another embodiment the invention provides a use of a vaccine composition in a method or a product of the invention.

In yet another embodiment the invention provides a use of an antigen, or a precursor thereof, for manufacturing a vaccine composition for vaccinating an animal or a human to obtain therein an immune response against said antigen, wherein said vaccine composition is administered sequentially with at least one other vaccine composition containing at least an immunogenic part, derivative and/or analogue of said antigen or antigen precursor, and a different vector.

As proof of principle we undertook a vaccine efficacy study comparing one vector system alone, two different combinations of two different vector systems, and the use of three different vectors administered sequentially. All vectors used to immunise animals expressed similar $SIV_{mac}$ antigens. Two months following the last immunisation animals were challenged intravenously with a highly pathogenic $SIV_{mac.1XC}$ inoculum and followed for evidence of protection.

EXAMPLES

Materials and Methods

Study Population

The study was carried out in outbred rhesus monkeys (*Macaca mulatta*). Four groups of 4 animals and 1 group of 3 animals (19 rhesus monkeys in total) were studied. Each animal was identified by a unique animal number tattooed on the chest. The animals were derived from Indian genetic stock and purpose bred in captivity either in the USA (groups A, B, C, D, E) or the Netherlands (group F). Their age ranged from 2.5 to 3 years (groups A, B, C, D, E) or 10 to 11 years (group F). Their weights ranged between 2.7 and 3.9 kg (groups A, B, C, D, E) or 5.2 to 9.1 kg (group F). The animals were negative for SIV, STLV, SRV and had no previous immunosuppressive treatment. During the experiment all animals were housed separately in individual cages.

Three different vector systems were utilised, each containing the same genetic information for SIV gag/pol, rev, tat, nef and env. The vectors consisted of a bacterial plasmid based DNA expression vector, modified Vaccinia Virus Ankara (MVA) and Semliki Forest Virus (SFV). The first group (A) consisted of four animals immunised with SIV-MVA chimerics alone. Secondly, the immune responses obtained after immunisation with the DNA expression vectors and two boosters with either MVA-SIV (group B) or SFV-SIV (group C) vectors were compared to those obtained with a triple vector strategy; priming by immunisation first with DNA expression vectors, 1st booster with the MVA-SIV constructs, then 2nd booster with the SFV-SIV constructs (group D). The virus loads (by quantitative RNA PCR) were studied before and after virulent SIV challenge. Animals were challenged intravenously with a cell-associated SIV challenge stock (1XC).

In addition to the animals vaccinated de novo, 3 monkeys protected from a previous SIV vaccine study served as protein primedî vector boost group (group F). They first received a boost with MVA-SIV, followed by SFV-SIV constructs.

Experimental Design

Group A: One group of 4 animals immunised three times with MVA vectors expressing SIV gag/pol, rev, tat, nef and env administered intramuscularly.

Group B: One group of 4 animals immunised first intradermally with the DNA vectors expressing SIV gag/pol, rev,. tat, nef and env, then boosted twice intramuscularly with MVA chimerics expressing similar SIV genes.

Group C: One group of 4 animals immunised with the DNA vectors expressing gag/pol, rev, tat, nef and env of SIV and boosted twice intravenously with SFV-SIV recombinant vectors expressing similar SIV genes.

Group D: One group of 4 animals vaccinated with the DNA expression vectors, boosted first with MVA-SIV chimerics and then with the SFV-SIV constructs.

Group E: One group of 4 control animals injected with empty DNA, and with the empty MVA and SPV vectors as infection controls.

Group F: One group of 3 animals which had proved to be protected from challenge in a previous study with a protein vaccine, then to be boosted first with the MVA-SIV chimerics, then with the SFV-SIV constructs.

DNA Expression Vector Based Vaccines

Vectors pTH.UbgagPk, pTH.UbpolPk, pTh.UbnefPk, pTH.tat, and pTH.rev express the gag, pol, nef, tat and rev genes of $SIV_{macJ5}$ (Rud et al., 1994) under control of the human cytomegalovirus immediate-early (hCMV IE) enhancer/promotor (Hanke et al., 1998a). The vector pTH and cloning sites have been described previously (Hanke et al., 1998a; 1998b) in which the hCMV enhancer/promotor/ intron A is cloned into the MIuI and HindIII sites and the individual SIVmacJ5 genes tat and cloned between HindIII and XbaI. Two vectors pTH.tat and pTE.rev contain the respective rev genes into the BamHI site without upstream Ub-R. The $SIV_{macJ5}$ molecular clone was used as the source of these genes as previously described (Rud et al., 1994; Rhodes, A. D. et al., 1994; and Hanke et al., 1994). Vector pND14G1 expresses the $SIV_{mac239}$ envelope gp120coding sequence under control of the hCMV IE enhancer/promotor and the simian D type retrovirus 1 (SRV-1) cis sequence was cloned between the gp120 gene and the BGH poly A/terminator region (Rhodes, G. H. et al., 1994; Indraccolo et al., 1998). All constructs contain the hCMV intron A sequence 5i of the expressed genes, in order to increase expression from the hCMV enhancer/promotor sequence, and carry the bovine growth hormone (BGH) polyA signal/ terminator sequence. Each different DNA vector SIV construct was administered separately at a dose of 50 μg of DNA in 200 μl of saline with ½ of the volume injected into two separate sites intradermally.

SFV Based Vaccines

The SFV based vaccines used in this study express the gag/pol, nef, tat, rev, and env proteins of $SIV_{mac32H\ J5}$. The gag/pol, env and nef coding sequences and the tat and rev cDNAs from the pJ5 molecular clone of the $SIV_{mac32H}$ proviral genome (Rud et al., 1994; Rhodes, A. D. et al., 1994) were subcloned in the pSFV1 vector (Liljestrom and Garoff, 1991). The gag/pol coding sequences were obtained by PCR amplification to flank these genes by BamHI suitable for subcloning in the pSFV1 vector (Zhang et al., 1997). For packaging of recombinant SFV (rSFV) viral stocks a two-helper system was used (Smerdou and Liljestrom, 1999). Virus titres were determined by infection of BHK cells in limiting dilutions followed by indirect immunofluorescence using antibodies directed against relevant SIV proteins. Expression of the SIV antigens in infected BHK cells was also demonstrated by western blot and immunoprecipitation analysis of metabolically labelled BHK21 cells.

MVA Based Vaccines

Modified Vaccinia Ankara (MVA) (Sutter and Moss, 1995) recombinants in this study express the gag/pol, nef, tat, rev, and env genes of $SIV_{mac\ J5}$ (Rud et al., 1994; Rhodes, A. D. et al., 1994) under transcriptional control of P7.5 vaccinia virus early/late promotor (Sutter et al., 1994). Briefly, the gag/pol, env and nef coding sequences and the tat and rev cDNAs from the $SIV_{macJ5}$ molecular clone (Rud et al., 1994; Rhodes et al., 1994) were subcloned in the MVA vector plasmid pIILzP7.5 at the SmaI site (Sutter and Moss, 1995; Sutter et al., 1994; and Seth et al., 1998) with the exception of env which was placed under control of a strong vaccinia vector promotor (Sutter et al., 1994). All of these reagents are stored and accessible through the NIBSC AIDS reagent repository, Potters Bar, U.K.

Vaccine Challenge Strain

The pathogenic, cell-associated SIV stock ($SIV_{mac32H.1XC}$) from primary, uncultured rhesus monkey PBMC "1XC", described previously (Niphuis et al., 1994), was used as the challenge virus also described in a previous vaccine study (Heeney et al., 1994).

Administration of the Vaccines

Rhesus monkeys were sedated with ketamin (10 mg/kg, prior to vaccine administration and bleedings. The vaccines were administered either intradermally (DNA vectors) or intramuscularly (MVA) or intravenously (SFV). In particular, 50 μg of each DNA expression vector in 200 μl of saline was administered per monkey, half of the volume injected into two separate sites. All immunisations with DNA were given twice at 12 week intervals followed by either MVA and/or SFV (see experimental design) at additional 12 week intervals.

Virus Challenge and Follow-up

All animals were challenged 2 months after the last immunisation with 50 $MID_{50}$ of the pathogenic cell-associated SIV stock "1XC" administered by the intravenous route (volume: 1 ml/monkey) (Niphuis et al., 1994). Post-challenge readouts included quantification of plasma viral RNA as described previously (Ten Haaft et al., 1998), and assessment of CD4 T-cell numbers in peripheral blood.

Results and Discussion

To determine if protective imuunity was obtained all animals were challenged with a highly pathogenic in vivo passaged rhesus PBMC stock of $SIV_{mac32H.1XC}$. As observed in FIG. 2E all of the control animals became readily infected (group E) with peak virus loads at two weeks reaching $5\times10^6$ and $5\times10^7$ RNA Eq/ml and remaining greater than $1\times10^4$ RNA Eq/ml 12 weeks post-infection. All animals in group A, which received MVA-SIV constructs alone, also became infected (Table 1), although one animal had lower peak virus loads and a load lower than $1\times10^4$ RNA Eq/ml by 6 weeks post-infection (FIG. 2A). All animals in group B which received DNA-SIV priming and MVA-SIV boosts also became infected (Table 1), with high virus loads persisting above pathogenic threshold levels ($>1\times10^5$ viral RNA Eq/ml) after challenge. In group C one out of four animals was protected (Table 1) from infection, although those which became infected were not protected from virus load (FIG. 2C).

Figure 2:
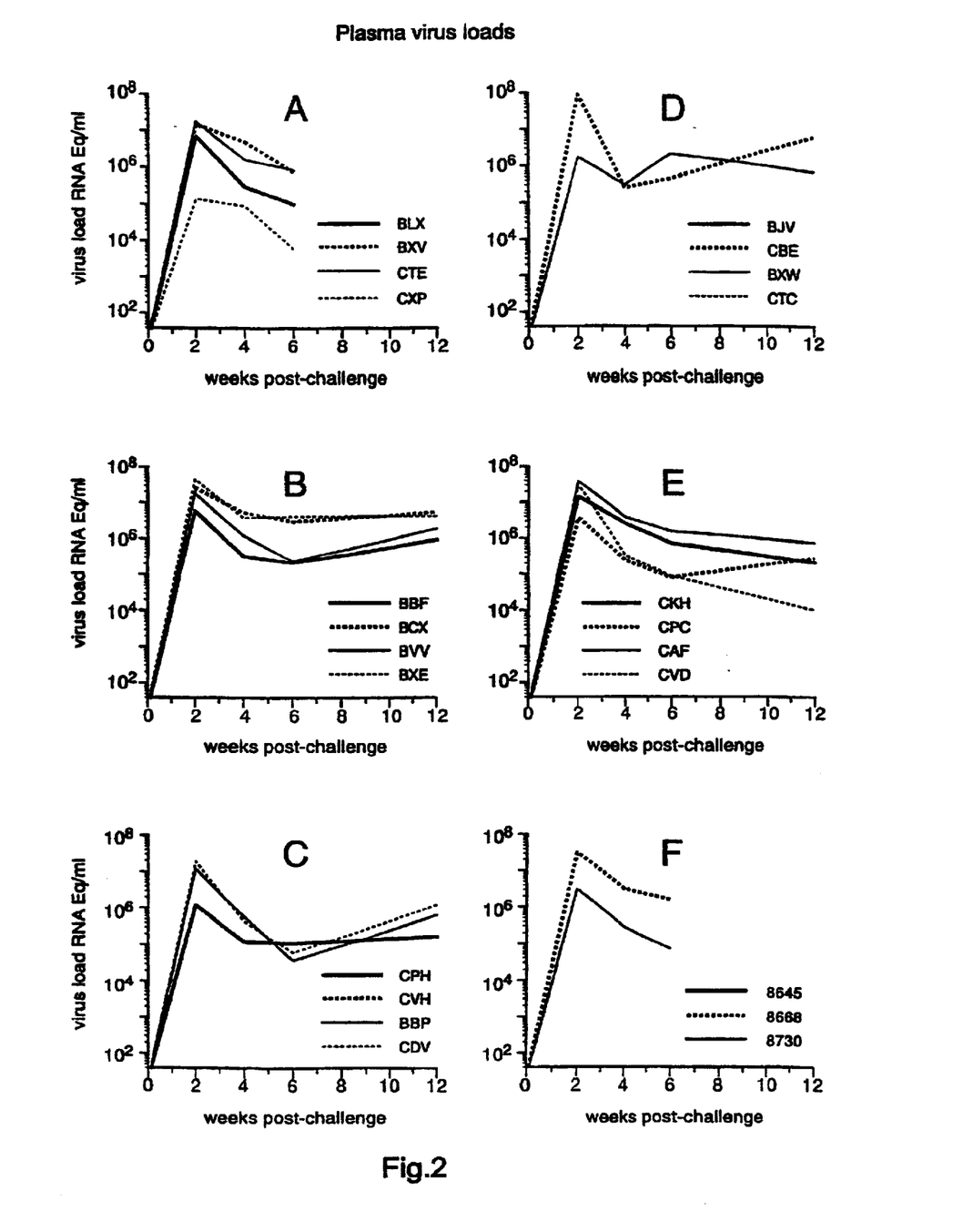

Satisfactory protection was observed in animals which received three different vaccine vectors (Table 1) (FIG. 2) with which protection from SIV challenge was obtained in 50% of the animals. Indeed, when subunit, protein vaccinated animals which were previously protected from challenge were boosted 5 years later with a combination of two vectors (Group F, Table 1), vaccine protection was still observed in one out of three animals. Data post-infection revealed that immunisation did not sufficiently protect from virusload (FIG. 2).

Improved protection against SIV infection was obtained when three vector systems were used (groups D, and F, Table. 1). In group D, immunised with three different vector systems, protection against infection was found in 2 out of four immunised animals (Table 1, FIG. 2D). Clearly, the use of one vector system alone for multiple immunisations was insufficient to protect from infection as in the case of MVA/SIV (group A) in this study (Table 1). This failure of protection from infection has been observed in other studies with SFV-SIV used alone for multiple immunisations (Mossman et al., 1996), although protection from acute symptoms (but not chronic disease) was suggested. A vaccine strategy using DNA priming and MVA boosting failed to protect immunised monkeys from infection (group B, Table 1). The use of DNA plus SFV to immunise showed limited promise in which one animal (group C, Table 1, FIG. 2C) was protected from infection.

Figure 3:
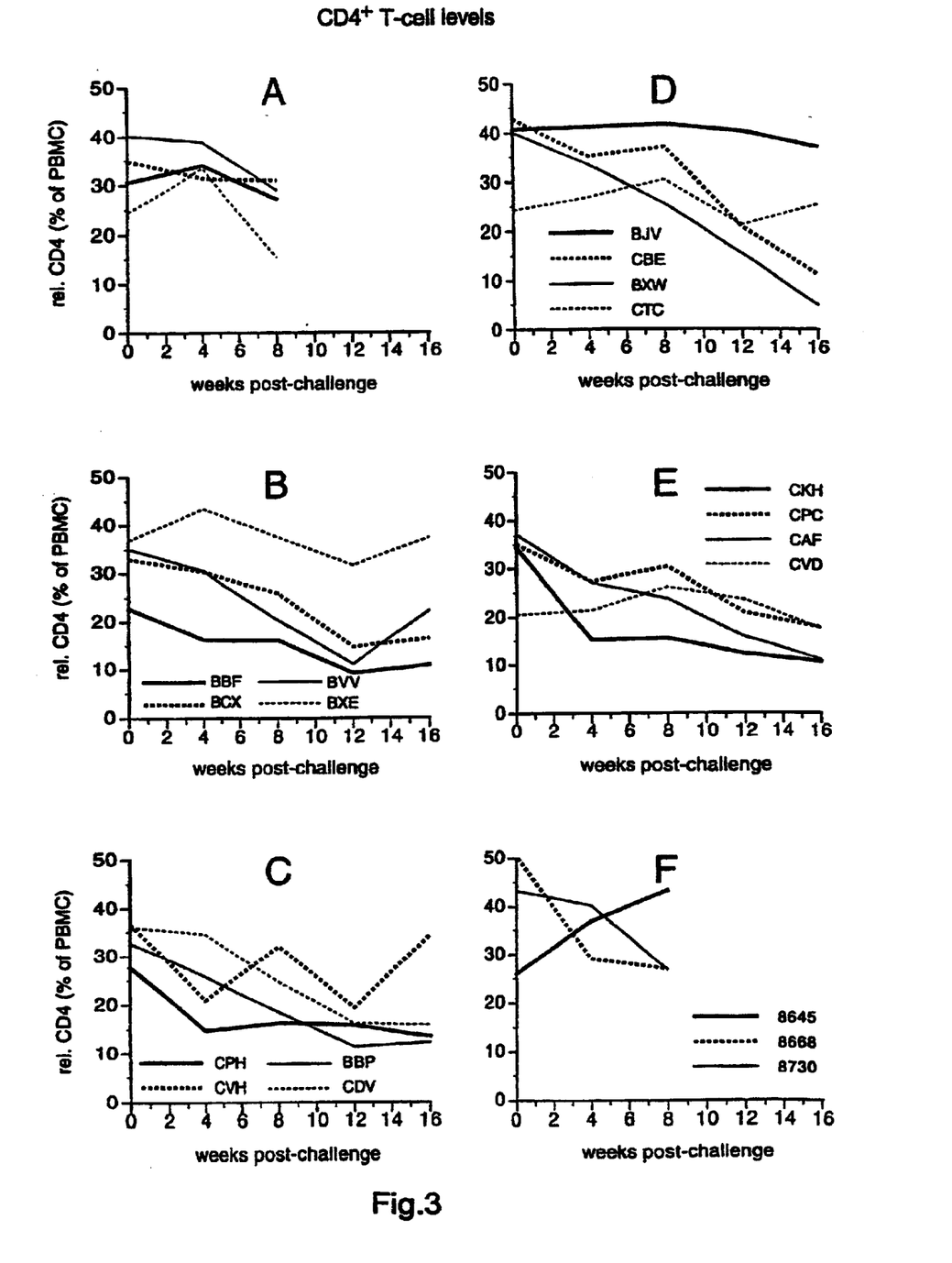

The best result against such potent challenges as the $SIV_{mac32H.1XC}$ used here was achieved with the use of three different vectors (group D, Table 1, FIG. 2D). Further proof was observed when the peripheral blood CD4⁺ T-cells numbers were examined (FIG. 3). The $SIV_{mac32H.1XC}$ used in this study causes a marked decline in CD4⁺ T-cell numbers over time as observed in the control group (E) (FIG. 3E) as well as other infected animals in this study. Notably, the animals which were protected from infection by the use of the triple vector strategy (animals BJV and CTC, group D) maintained normal CD4⁺ T-cell levels while those of the infected animals declined. This was also noted in the protected animal (8645) in group F (FIG. 3F) which has received a triple combination of a protein immunisation followed by MVA and SFV, further supporting this, concept.

Through further refinement of this strategy, using combinations of different or divergent chimeric vectors, is improved levels of vaccine protection are likely. Furthermore, optimisation of different combinations of vector systems delivered to different sites and populations of antigen presenting, cells will lend this application to mucosal and/or combined mucosal/systemic vaccine strategies. It is envisioned that in addition differential modulation of immune responses (i e. innate and, specific such as type 1 vs type 2 $T_H$ responses) and the induction of potent immunological memory will be possible using combinations of different vaccine vector systems.

TABLE 1

Experimental group and outcome

| Group | "prime" | 1st boost | 2nd boost | protected |
|---|---|---|---|---|
| A | MVA-SIV | MVA-SIV | MVA-SIV | 0/4 |
| B | DNA-SIV | MVA-SIV | MVA-SIV | 0/4 |
| C | DNA-SIV | SFV-SIV | SFV-SIV | 1/4 |
| D | DNA-SIV | MVA-SIV | SFV-SIV | 2/4 |
| E | DNA | MVA | SFV | 0/4 |
| F | W. Virus protein "protected" | MVA-SIV | SFV-SIV | 1/3 |

BRIEF DESCRIPTION OF THE DRAWINGS

FIG. 1:

A diagram comparing; (A) existing immunisation strategies with one delivery (i.e. vector) system; (B) the proposed combination of delivery (i.e., multiple vectors) systems. Immune responses to the desired Antigen are optimised and intensified with subsequent boosting with the combination strategy (B) as compared to conventional single delivery systems (A).

FIG. 2

A comparison of plasma RNA virus loads in immunised and control animals which became infected after challenge with SIV. FIG. 2A shows the virus loads in animals which had been immunised repeatedly with the same vector (3×MVA). FIG. 2E shows the plasma virus loads in the control animals ewhich were not immunised with any SIV antigen. Post-challenge virus loads for each of the other combination groups; B (DNA, 2×MVA), C (DNA, 2×SFV), D (DNA, MVA, SFV) and F (protein, MVA, SFV) respectively.

FIG. 3

Comparison of CD4$^+$ T-cell levels following challenge per group. In infected animals CD4$^+$ T-cells declined as was especially evident in the control animals (E). The CD4$^+$ T-cell levels can be observed to remain at normal levels in protected animals, especially BJV and CTC in group D (D) which received the combination immunisation protocol. Groups depicted; A (3×MVA), B (DNA, 2×MVA), C (DNA, 2×SFV), D (DNA, MVA, SFV) E (controls), F (protein, MVA, SFV), respectively.

LITERATURE

Berglund, P., Quesada-Rolander, M., Putkonen, P., Biberfeld, G., Thorstensson, R., Liljestrom, P. Outcome of immunisation of cynomolgus monkeys with recombinant Semliki Forest virus encoding human immunodeficiency virus type 1 envelope protein and challenge with a high dose of SHIV-4 virus. AIDS Res.Hum Retroviruses 1997, 13 (17): 1487–1495.

Haaft, P. ten, Verstrepen, B., Uberla, K., Rosenwirth, B., Heeney, J. L. A pathogenic threshold of virus load defined in Simian Immunodeficiency Virus- or Simian-Human Immunodeficiency Virus-infected macaques. J. Virology, 1998, 72 10281–10285.

Hanke, T. et al., Expression and purification of nonglycosylated SIV proteins, and their use in induction and detection of SIV-specific immune responses. AIDS Res. Hum. Retroviruses 1994, 10(6): 665–674.

Hanke, T., Blanchard, T. J., Schneider, J., Hannan, C. M., Becker, M., Gilbert, S. C., Hill, A. V., Smith, G. L. McMichael, A. Enhancement of MHC class I-restricted peptide-specific T cell induction by a DNA prime/MVA boost vaccination regime. Vaccine 1998a, 16(5): 439–445b.

Hanke, T., Schneider, J., Gilbert, S. C., Hill, A. V., McMichael, A. DNA multi-CTL epitope vaccines for HIV and Plasmodium falciparum: immunogenicity in mice. Vaccine 1998b, 16(4): 426–435.

Heeney, J. L., Els, C. van, Vries, P. de, Haaft, P. ten, Otting, N., Koornstra, W., Boes, J., Dubbes, R., Niphuis, H., Dings, M., Cranage, M., Norley, S., Jonker, M., Bontrop, R.E., Osterhaus, A. MHC class I associated vaccine protection from SIV infected peripheral blood cells. J Exp Med, 1994, 180: 769–774.

Indraccolo, S., Feroli, F., Minuzzo, S., Mion, M., Rosato, A., Zamarchi, R., Titti, F., Verani, P., Amadori, A., Chieco-Bianchi, L. DNA immunisation of mice against SIV-mac239 Gag and Env using Rev-independent expression plasmids. AIDS Res. Sum. Retroviruses 1998, 14(1): 83–90.

Liljestrom, P., Garoff, H. A new generation of animal cell expression vectors based on the semliki forest virus replicon. BioTech. 1991, 9: 1356–1361.

Mossman, S. P., Bex, F., Berglund, P., Arthos, J., OíNeil, S. P., Riley, D., Maul, D. H., Bruck, C., Momin, P., Burny, A., Fultz, P. N., Mullins, J. I., Liljestrom, P., Hoover, E. A. Protection against lethal simian immunodeficiency virus SIVsmmPBj14 disease by a recombinant Semliki Forest virus gp160 vaccine and by a gp120 subunit vaccine. J. Virol. 1996, 70 (3): 1953–1960.

Niphuis, H., Dubbes, R., Haaft, P. J. F. ten, Koornstra, W. H., Bontrop, R. E., Cranage, M. P., Heeney, J. L. Infectivity and virulence of cell-associated SIVmac after single passage in vivo. AIDS, 1994, 8: 1730–1731.

Rhodes, A. D. et al., Expression, characterization and purification of simian immunodeficiency virus soluble, oligomerized gp160 from mammalian cells. J. Gen. Virol 1994, 75: 207–213.

Rhodes, G. H., Abai, A. M., Margalith, M., Kuwahara-Rundell, A., Morrow, J., Parker, S. E., Dwarki, V. J. Characterization of humoral immunity after DNA injection. Dev. Biol. Stand. 1994, 82; 229–236.

Rud, E. W. et al., Molecular and biological characterization of simian immunodeficiency virus macaque strain 32H proviral clones containing nef size variants. J. Gen. Virol. 1994, 75: 529–543.

Schneider, J., Gilbert, S. C., Blanchard, T. J., Hanke, T., Robson, K. J., Hannan, C. M., Becker, M., Sinden, R., Smith, G. L., Hill, A. V. Enhanced immunogenicity for CD8$^+$ T cell induction and complete protective efficacy of malaria DNA vaccination by boosting with modified vaccinia virus Ankara. Nat. Med. 1998, 4(4): 397–402.

Seth, A., Ourmanov, I., Kuroda, M. J., Schmitz, J. E., Carroll, M. W., Wyatt, L. S., Moss, B., Forman, M. A., Hirsch, V. M., Letvin, N. L. Recombinant modified vaccinia virus Ankara-simian immunodeficiency virus gag pol elicits cytotoxic T lymphocytes in rhesus monkeys detected by a major histocompatibility complex class I/peptide tetramer. Proc. Natl. Acad. Sci. U.S.A. 1998, 95(17): 10112–10116.

Smerdou, C., Liljestrom, P. Two-helper RNA system for production of recombinant semliki forest virus particles. J. Virol. 1999, 73(2): 1092–1098.

Sutter, G., Moss, B. Novel vaccinia vector derived from the host range restricted and highly attenuated MVA strain of vaccinia virus. Dev. Biol. Stand 1995, 84: 195–200.

Sutter, G., Wyatt, L. S., Foley, P. L., Bennink, J. R., Moss,. B. A recombinant vector derived from the host range-restricted and highly attenuated MVA strain of vaccinia virus stimulates protective immunity in mice to influenza virus. Vaccine 1994, 12(11): 1032–1040.

Zhang, J., Asselin-Paturel, C., Bex, F., Bernard, J., Chehimi, J., Willems, F., Caignard, A., Berglund, P., Liliestrom, P., Burny, A., Chouaib, S. Cloning of human IL-12 p40 and p35 DNA into the Semliki Forest virus vector: expression of IL-12 in human tumor cells. Gene Ther. 1997, 4 (4): 367–374.

What is claimed is:

1. A method for inducing or stimulating a T-helper cell response in a human or animal against at least one antigen, comprising the steps of:

i. administering a first immunogenic composition comprising a first vector encoding said antigen;

ii. administering a second immunogenic composition comprising a second vector encoding said antigen and;

iii. administering a third immunogenic composition comprising a third vector encoding said antigen;

wherein the first, second and third vectors are not the same and are chosen to avoid repeated exposure of vector proteins or vector encoded proteins;

wherein the first, second and third immunogenic compositions are administered sequentially to the animal or human;

wherein at least part of said vectors functions as an adjuvant; and wherein the antigen is an antigen of a lentivirus.

2. The method according to claim 1, wherein the lentivirus causes a temporary or long lasting immune impairment.

3. The method according to claim 1, wherein said adjuvant function directs the immune response toward a more T helper 1 type or a more T helper 2 type of response or both.

4. The method according to claim 1, wherein said antigen comprises at least an immunogenic part, derivative and/or analogue of a lentivirus gag, pol, rev, tat, nef or env protein or a combination thereof.

5. The method according to claim 1, wherein at least one of said immunogenic compositions comprises a nucleic acid encoding at least one proteinaceous molecule capable of inducing and/or boosting an immune response against said antigen.

6. The method according to claim 5, wherein said proteinaceous molecule comprises said antigen, or an immunogenic part derivative or analogue thereof.

7. The method according to claim 5, wherein said nucleic acid comprises a nucleic acid selected from the group consisting of a Semliki Forest Virus, a poxvirus, a herpesvirus and an adenovirus, or a combination thereof.

8. The method according to claim 5, wherein said proteinaceous molecule is selected from the group consisting of a co-stimulatory protein; an immune response inhibitory protein, an interleukin, a major histocompatibility complex protein and a functional part derivatives and/or analogues thereof.

9. The method according to claim 1, wherein said first, second, and/or third vector comprises a nucleic acid which encodes at least one proteinaceous molecule capable of modulating an immune response.

10. The method according to claim 1, wherein said first, second, and/or third vector is a nucleic acid delivery vehicle comprising said nucleic acid.

11. The method according to claim 10, wherein said nucleic acid delivery vechicle is selected from the group consisting of a Semliki Forest Virus particle, a pox virus particle, a herpes virus particle and an adenovirus particle.

* * * * *

UNITED STATES PATENT AND TRADEMARK OFFICE
CERTIFICATE OF CORRECTION

PATENT NO. : 6,783,762 B1
DATED : August 31, 2004
INVENTOR(S) : Heeney

It is certified that error appears in the above-identified patent and that said Letters Patent is hereby corrected as shown below:

Column 9,
Line 50, now reads "imuunity", and should read -- immunity --.

Column 11,
Line 17, now reads "ewhich", and should read -- which --.

Signed and Sealed this

Seventh Day of December, 2004

JON W. DUDAS
*Director of the United States Patent and Trademark Office*